United States Patent [19]
Cody et al.

[11] Patent Number: 4,824,016
[45] Date of Patent: Apr. 25, 1989

[54] ACOUSTIC MONITORING OF TWO PHASE FEED NOZZLES

[75] Inventors: George D. Cody, Princeton, N.J.; Craig A. Joseph, Oakland; Uri Sela, Walnut Creek, both of Calif.; Charles L. Baker, Baton Rouge, La.

[73] Assignee: Exxon Research and Engineering Company, Florham Park, N.J.

[21] Appl. No.: 131,366

[22] Filed: Dec. 10, 1987

[51] Int. Cl.⁴ .............................................. G01H 3/00
[52] U.S. Cl. .......................................... 239/8; 239/61; 239/71; 73/861.18
[58] Field of Search ...................... 239/1, 8, 61, 71; 73/168, 861.04, 861.18, 865.9

[56] References Cited

U.S. PATENT DOCUMENTS

| | | | |
|---|---|---|---|
| 3,816,773 | 6/1974 | Baldwin et al. | 73/861.04 |
| 4,019,653 | 4/1977 | Scherer et al. | 239/61 |
| 4,357,603 | 11/1982 | Roach et al. | 73/861.21 |

FOREIGN PATENT DOCUMENTS

2156520 10/1985 United Kingdom .

Primary Examiner—Andres Kashnikow
Assistant Examiner—Karen B. Merritt
Attorney, Agent, or Firm—Ronald D. Hantman

[57] ABSTRACT

Passive acoustic method for monitoring and controlling flow state of two phase fluids through feed nozzles and thereby improving operating stability and high product value yields in major refinery processes or any other process where a finely atomized liquid stream exiting the nozzle is important.

6 Claims, 10 Drawing Sheets

ACOUSTIC MONITORING OF TWO PHASE FEED NOZZLES

The present invention relates to a process to monitor and control feed atomization in fluidized bed reactors or transfer lines. Petrochemical processes that depend on fluidized beds or transfer lines include the thermal cracking of heavy oils in processes described as "fluid bed coking" or "flexicoking", and the catalytic cracking of complex hydrocarbons in the process called "catalytic cracking" or "cat-cracking". Such processes are major components of modern refineries which use them to convert more and more difficult feedstocks into petroleum products of great added value.

One key component of either fluid bed coking or cat cracking is the feed nozzle. Feed nozzles are designed to finely atomize heavy oil in order to allow dispersion of a thin, uniform oil layer on approximately 150 micron coke particles (fluid bed coking) or approximately 60 micron catalyst particles (cat cracking). Maintaining the performance of these feed nozzles through the multi-year running cycle of a refinery is very important to operating stability and high value product yields However, maintaining the performance of these feed nozzles can be complicated by several factors. For example the oil feed to the feed nozzles is typically very viscous and the composition of the oil is highly variable. Under these conditions, small changes in the temperature of the oil feed can have a dramatic effect on the performance of the nozzle. Furthermore, the feed nozzle is inserted in a harsh environment where erosion by particles and plugging by process deposits can both adversely affect feed nozzle performance. In addition the feed nozzles usually receive feed and steam from manifolds that supply a multiplicity of feed nozzles. Under these circumstances it is difficult, if not impossible, to ensure that each nozzle is carrying a desired flow without monitoring the specific nozzle.

Of equal importance, is the fact that the feed nozzles used in fluid bed coking and cat cracking contain a two phase mixture of non-ideal fluids namely steam and heavy oil. Because of the non-ideal nature of these mixtures, feed nozzles typically operate in a number of flow regimes These range from the desired stable flow regime where the steam and oil are finely mixed to provide the desired atomization, up to the undesirable flow regime where steam and oil are alternately passed through the nozzle with very little mixing ("slugging").

Two of the major factors involved in obtaining a desired flow characteristic for a feed nozzle are: (1) the amount of steam injected into the feed nozzle with the heavy oil and (2) the supply pressure of the heavy oil to the feed nozzle. Steam usage in heavy oil feed nozzles performs two functions. Firstly, it keeps the feed nozzle clear from blockage when the feed oil is removed from the nozzle. Secondly, and most importantly, it disperses the heavy oil feed into fine droplets that improve the contact between the feed oil and the coke or catalyst particles. However, since the steam introduces a highly compressible component into the oil, its presence has a major effect on the hydrodynamics of the steam/oil mixture and, therefore introduces a high degree of uncertainty into feed nozzle design. The volume of steam to volume of oil ratio used in a particular nozzle design is a key factor in obtaining a desired feed nozzle flow characteristic. This steam to oil ratio can be affected by a number of different operating conditions including feed viscosities. The supply pressure of the heavy oil feed can have a major effect on the nozzle flow characteristics as well as flow instabilities of feed nozzles supplied by a common oil manifold.

In general, obtaining and maintaining designed feed atomization is a difficult task and one that is of major importance. In fluid bed cokers, poor atomization can lead to immediate local defluidization and the formation of large agglomerates which can reduce circulation. In the extreme, so many agglomerates are formed that the entire bed may collapse. Poor feed atomization is also considered a cause of excessive build up of wall coke in cokers. Run limiting "upsets" of the process are often the result of the spalling of large chunks of coke which fall into critical regions of the circulation system and disrupt the flow. In cat crackers feed atomization has a direct effect on process yield and product composition.

Until recently, ensuring that feed nozzles are operating in the desired flow regime, and maintaining that condition under changes in feed and process conditions has been a matter of trial and error. For example nozzles could be routinely "rodded out" or mechanically cleaned. There has been no way of verifying on an operating unit, the flow regime of the nozzle since there was no direct tool to monitor flow. It has now been found, and this is the subject of this patent application, that vibrational monitoring of feed nozzles (referred to in this patent as passive acoustic nozzle monitoring) can give quantitative information on the fluid state exiting the nozzle. A well atomizing nozzle can be easily distinguished from one that is plugged, or that is exhibiting slug flow. Based on the technique of passive acoustic nozzle monitoring, operators of a fluid bed coker or cat cracker can take appropriate actions to restore the desired operating conditions. These actions could include changing the relative ratios of oil and steam, rodding or cleaning out the nozzle or isolating a "bad nozzle" from the feed distribution system.

SUMMARY OF THE INVENTION

The present invention is a passive acoustic process whereby the current operating state of a feed nozzle injecting a mixture of liquid and gas into a process vessel can be non-intrusively determined using the natural occurring energy in the nozzle to set up a recognizable signature of vibrational resonances which can then be compared to a the vibrational signature o the desired operating state of the feed nozzle If there is a significant difference, corrective actions, such as cleaning the nozzle or changing the relative proportions of the liquid and gas, can be undertaken. The effect of such corrective actions to restore the nozzle to its desired operating conditions will be verified by repeating the same passive acoustic process. The process is a passive acoustic process since it senses the naturally occurring vibrations that are generated by the nozzle in its performance. In many commercial situations of interest to the petrochemical industry the feed the nozzle will be injecting is comprised of oil and steam. However, the invention can have wider application in any situation where it is important to maintain specified flow conditions through an injecting nozzle carrying a gas-liquid mixture including particulate laden liquids such as slurries and where the reliability of the gas supply can be poor such as orifice limiting systems. It is particularly applicable to manifolded systems where the nozzles are fed by a common manifold and where the piping to the nozzle is complex due to economic constraints. Under these circumstances it is difficult, if not impossible, to achieve a specified flow through each nozzle without individual monitoring and "tuning".

In a feed nozzle where oil and steam mix and are propelled out of the nozzle by the pressure drop across the nozzle, there can exist a variety of vibratory resonances in the volumes defined by regions of restricted or turbulent flow, including the nozzle tip. These resonances are concentrations of vibrational energy in the fluid or the structure of the nozzle in certain frequency ranges and result from the excitation of the acoustic and vibratory modes of the two phase fluid nozzle system. The multiplicity of vibratory resonances of variable intensity that occur over a given frequency range with different magnitudes constitute a signature in the power spectrum of the nozzle The power spectrum itself can be obtained in a variety of ways. For example in one embodiment of this patent, we utilize spectral analysis of the electrical output of an accelerometer in contact with the physical structure of the nozzle or of the electrical output of a dynamic pressure transducer in contact with the two phase flow within the nozzle. From the mathematical and vibrational literature, it is conventional to display in the power spectrum the mean square acceleration per unit frequency range as a function of frequency, however any mathematical function of the mean square acceleration per unit frequency range can be utilized to obtain such a suitable power spectrum although some representations will be found to be more convenient than others.

We have discovered that this power spectrum is stable in time as long as the flow state of the fluid exiting the nozzle is constant and that it can thus function as a two dimensional "signature" or "fingerprint" of the fluid state exiting the nozzle. Changes in the flow state of the nozzles brought about by changes in the nozzle tip or bore ("plugging") or by changes in the fluid inputs ("slugging") can be detected and corrected by appropriate procedures to return the power spectrum to that corresponding to the desired flow state. Furthermore, the power spectrum can be used to confirm that the corrective action has produced a return to the desired flow state. Recognition of significant changes in the power spectrum can be accomplished by a human observer in the case of periodic nozzle monitoring or by suitable pattern recognition algorithms in the case of continuous or real time nozzle monitoring. Furthermore, the power spectrum can be obtained simply and nonintrusively while the nozzle is operating. Examples of the correlation between the power spectrum of a particular nozzle and different flow conditions from that nozzle will be discussed below. The frequency range of the power spectrum is chosen so that resonances generated by the energy of the operating noise of the nozzle dominate the power spectrum.

It is surprising indeed that it is possible to find a frequency range where meaningful information can be obtained about nozzle flow conditions that is not masked by the background noise level of the reactor.

Under certain flow conditions additional information can be obtained from the time variation of the vibratory signal. For example, the fluid exiting the nozzle can be regularly alternating its flow (state e.g. intermittent slugging or sputtering or just unsteady flow). This is an undesired state of flow and as such will exhibit itself in changes in the power spectrum. The power spectrum is the fourier transform of the time variation of vibrating signal. However, it will also be a recognizable feature of the time variation of the vibrational signal and this time signature can be used to complement the information contained in the power spectrum. Again, examples of the correlation between certain time signatures and the flow states of the fluid exiting the nozzle will be given below.

The passive acoustic nozzle monitoring process includes the following steps:

1. A reference power spectrum (Reference Power Spectrum or RPS) is obtained from a vibrational sensor in close proximity to the nozzle or the fluid contained within when the nozzle is atomizing feed in the desired manner. This Reference Power Spectrum (RPS) is specific to a nozzle of specified mechanical dimensions and fluid connections and has to be determined empirically because of the well known complexity of two phase flow. Clearly under steady state conditions the RPS will not change. In the present patent the vibrational sensor is either an accelerometer attached to the nozzle shell or a pressure transducer in contact with the fluid within the nozzle. The frequency range over which the power spectrum is plotted is chosen empirically so that the vibrational resonances that characterize the power spectrum are dominated by energy produced by nozzle flow.

2. Subsequent current power spectra (Current Power Spectrum or CPS) are taken in either real time by a hard wired system monitored by a computer or taken periodically by operating personnel at the specific nozzle.

3. Comparison of the RPS with the CPS is made either by suitable computer pattern recognition algorithms or visually by personnel and changes noted.

4. Changes in the operating conditions of a specific nozzle are then made to restore the CPS to the RPS.

5. The time variation of the vibratory signal that accompanies the taking of the both the RPS and the CPS can be noted and used either by a suitable computer algorithm or by observation of personnel to supply complementary information on the variation of the state of fluid flow within nozzle within the measurement time.

DESCRIPTION OF THE PREFERRED EMBODIMENT

The present invention gives a method for nonintrusively determining if the liquid-gas mixture exiting a nozzle has departed from desired operating conditions. If it has, then the operating conditions of the nozzle are changed to return to the desired flow conditions, or the nozzle is cleaned, or removed from service. The method of the present invention will be illustrated and described by a heavy feed fluid bed thermal conversion process such as in a fluid bed coker where the nozzle contains feed oil and steam. However it is not limited to petrochemical applications but to situation where it is difficult to directly monitor flow through a specific nozzle and where the fluid being carried, or the nozzle environment leads to a high probability of unreliable nozzle performance.

Figure 1:
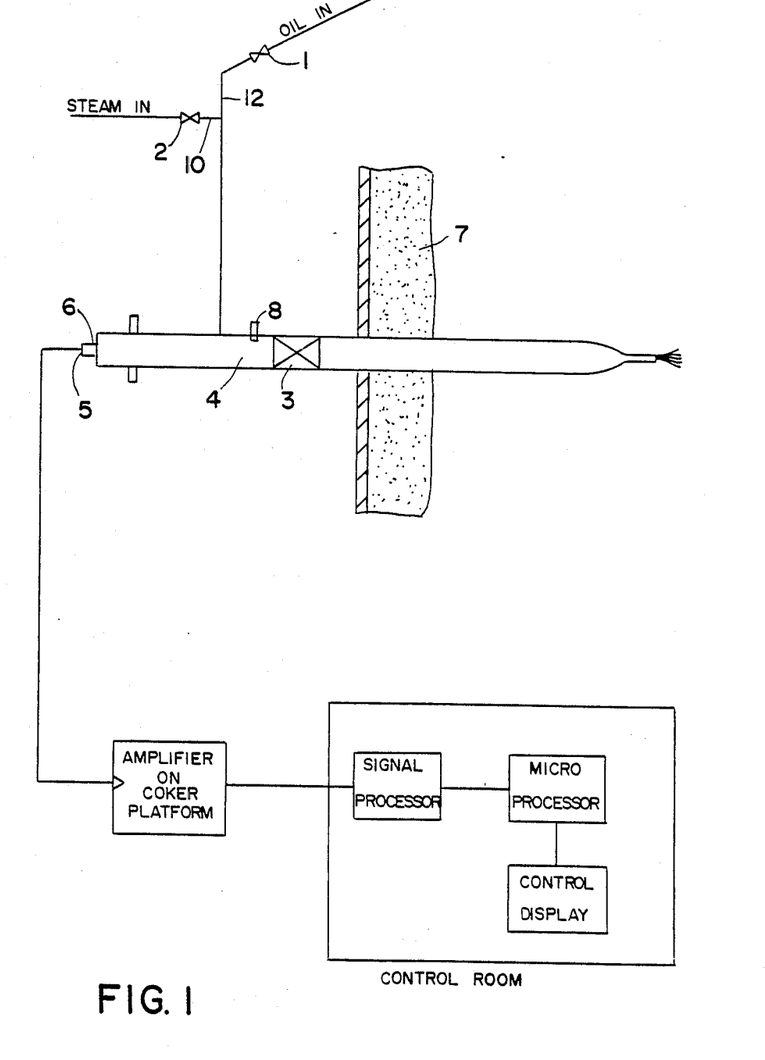
FIG. 1 shows a schematic diagram of the system according to the method of the claimed invention.

FIG. 1 shows a schematic diagram of a representative coker feed nozzle 4 inserted through a coker wall 7. Fluid bed cokers can contain anywhere from twenty to sixty such nozzles injecting feed at the rate of approximately ten to fifty gallons a minute. In one embodiment of the invention, an accelerometer 5 is placed in close proximity to the nozzle 4. In FIG. 1, the accelerometer 5 is placed on the rodding plug 6, but any location in proximity to the nozzle and where the accelerometer is sensitive to changes in flow conditions is acceptable.

Figure 2:
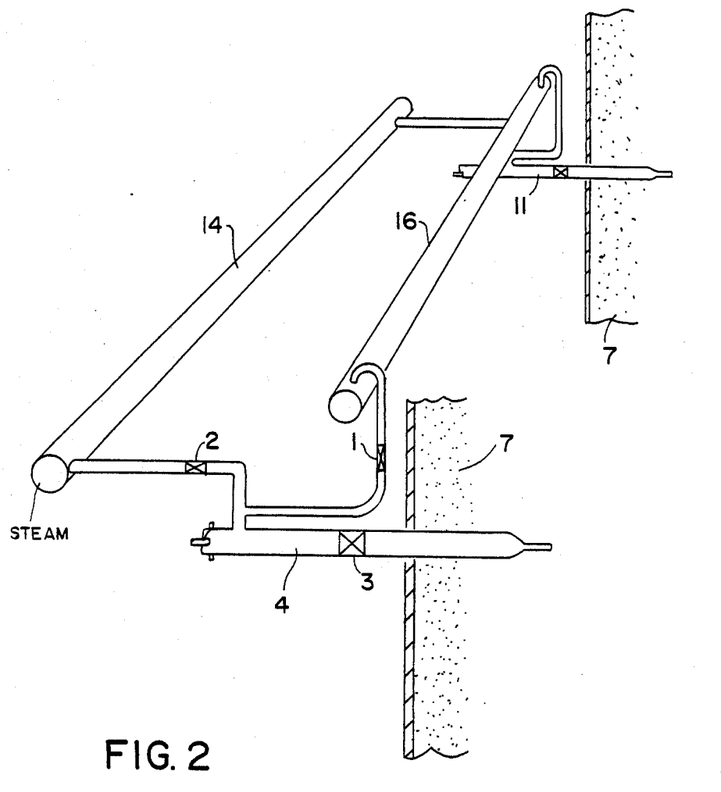
FIG. 2 shows a schematic figure of two nozzles being fed oil and steam through common headers.

As shown in FIG. 2, for a given reactor, several nozzles 4 and 11 may be interconnected so that steam and oil are supplied through a steam header 14 and oil header 16 to all nozzles simultaneously. In this case, the performance of one nozzle (upstream) can affect the power spectra observed for another (discussed below).

The electrical signal for the accelerometer is proportional to the nozzles vibration intensity and a plot of the mean square acceleration per unit frequency range or simple mathematical operations on this quantity (e.g. taking the square root of this quantity and multiplying by a constant to form a plot of the root mean square acceleration or taking the logarithm of the quantity to form a "db" plot) is an appropriate power spectrum for the purpose of this patent. In one use the sensor signal is amplified and transmitted by an appropriate data link to a control room as shown in FIG. 1. In the control room, the signal is processed by a spectrum analyzer or fast fourier transform signal processor. Also in the control room by an appropriate algorithm, the RPS is displayed and stored in memory. Similarly current power spectra or CPS are taken in real time and by a suitable pattern recognition algorithm compared to the RPS. Changes between the CPS and the RPS are brought to the attention of the operator to indicate changes in the flow regime of a specific nozzle for subsequent correction.

To assist the operator in interpreting the changes in the CPS from the RPS, a "dictionary" of characteristic CPS associated with specific flow conditions can be contained in memory and displayed to indicate the direction of changes to be made. Again the "dictionary" is feed nozzle specific and has been generated empirically due to the well known complexity of two phase flow in complex piping. The determination of a dictionary is illustrated and described below.

In addition an analysis of the time variation of the real time signal from the accelerometer sensor (time signature) is used to detect the presence of unstable flow during the measurement time.

Alternatively, the vibratory signal from the accelerometer can be processed at the nozzle by a portable spectrum analyzer operated by a technician and changes in the CPS from the RPS noted and corrective action taken with respect to a nozzle can be taken immediately at the nozzle location.

In another embodiment of the patent, the accelerometer 5 is replaced by a dynamic pressure transducer 8 in contact with the fluid In this case, the transducer penetrates the rodding plug to contact the fluid. Alternately, the transducer 8 may be located elsewhere along the nozzle (see FIG. 1). The frequency dependent pressure can be used to generate a power spectrum to serve as an RPS or a CPS.

Figure 3:
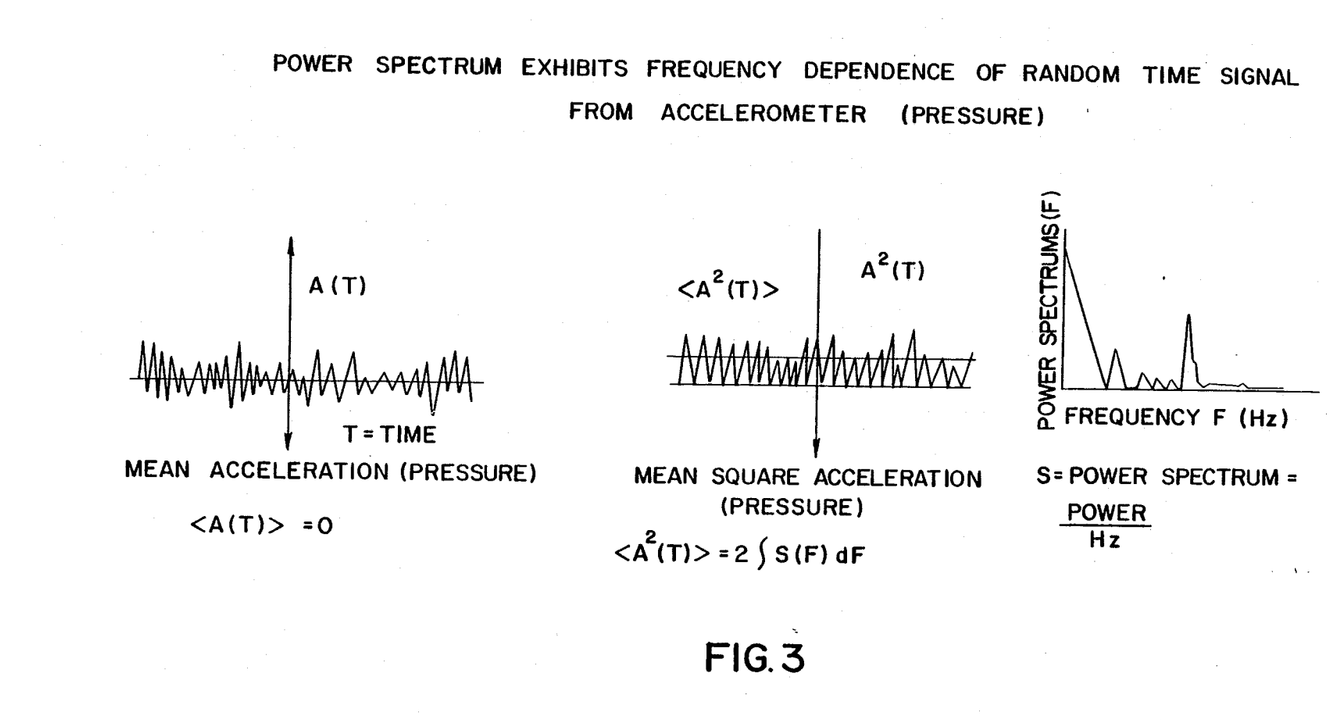
FIG. 3 shows the relationship between signal measured from the accelerometer and the power spectrum

FIG. 3 exhibits the relationship between the time varying electrical signal produced either by an accelerometer in contact with the mechanical shell of a feed nozzle or a pressure transducer in contact with the two phase mixture within the nozzle and the frequency distribution of the vibrational energy generated by the nozzle in its operation. It also shows the square of that signal as a function of time and frequency and exhibits the well known relationship between the area under the power spectrum and the mean square signal (mean square acceleration or mean square pressure fluctuation when the transducers are correctly calibrated) produced by the vibrational sensor.

Determining Of Dictionary For a Nozzle

A dictionary for a given nozzle is obtained by doing a power spectrum analysis for different flow conditions. FIG. 4 shows a sequence of power spectra of a nozzle for changes in flow conditions as induced by oil flow changes by valve (1) in FIG. 1 or steam flow changes by valve 2 in FIG. 1, or conditions of nozzles upstream on the same oil and steam headers.

Figure 4A:
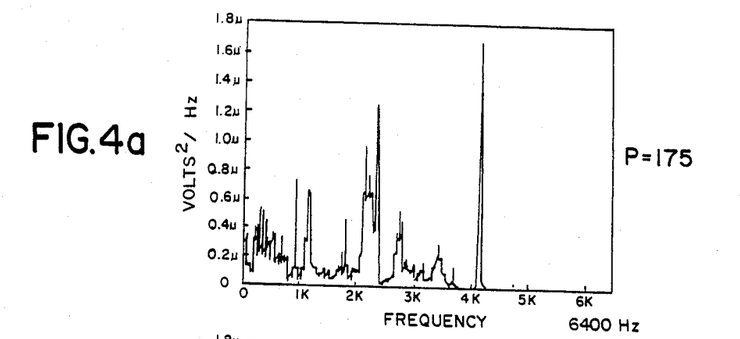
FIGS. 4a-h show the variation of the power spectrum as the flow conditions of a nozzle vary. The ordinate is in (volts)$^2$/Hz. The abscissa is in Hz. All pressures, P, are in PSI.
Figure 4B:
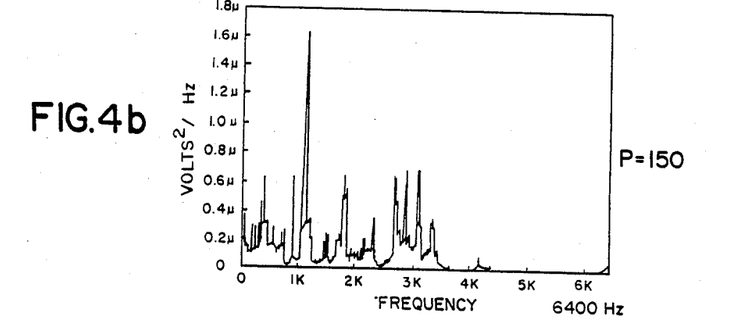
Figure 4C:
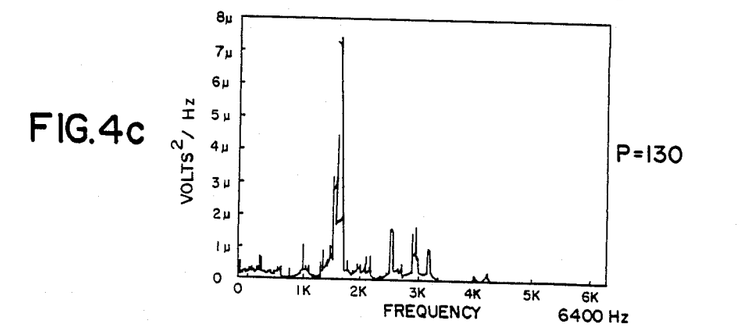
Figure 4D:
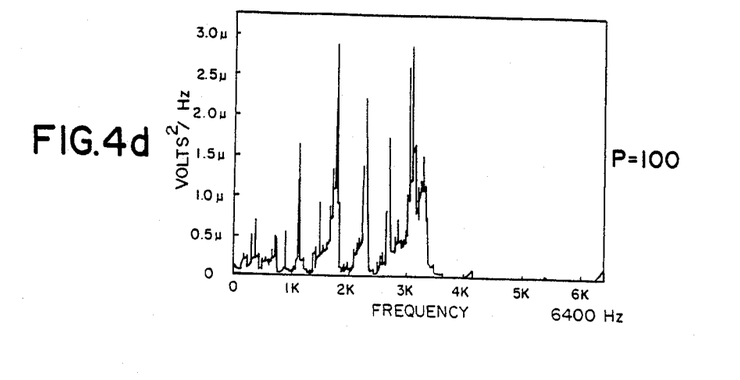
Figure 4E:
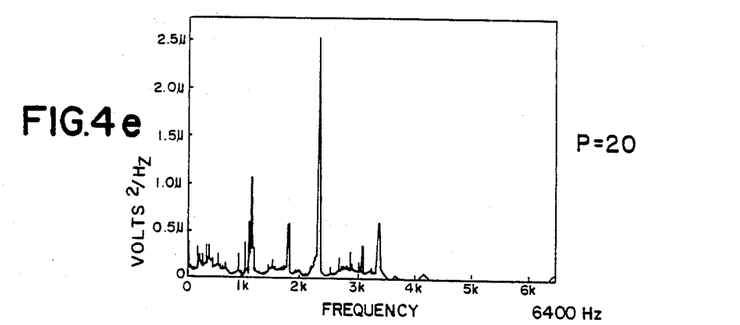
Figure 4F:
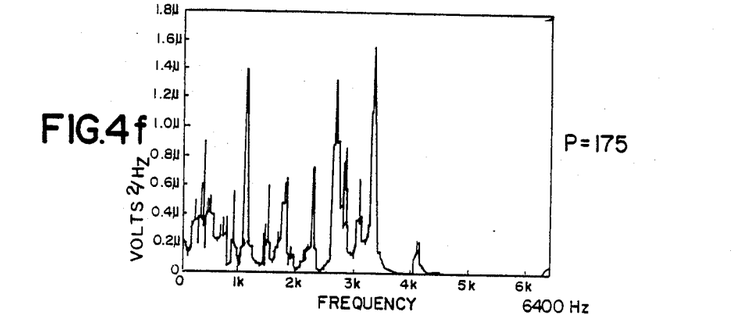
Figure 4G:
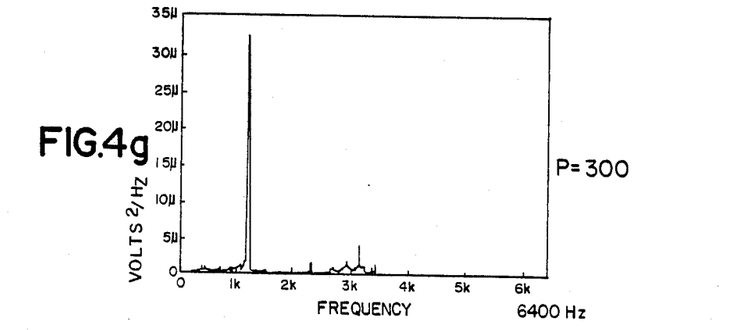
Figure 4H:
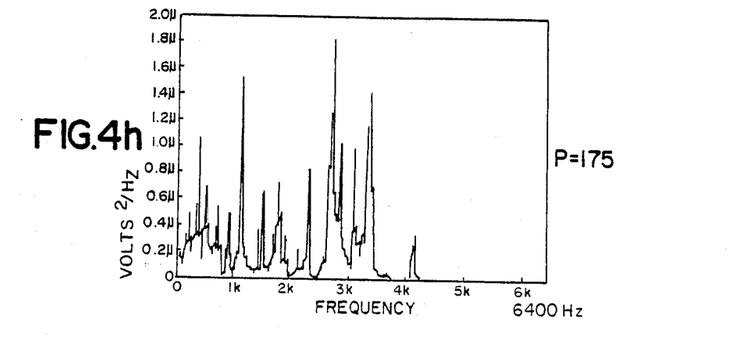

FIG. 4(a). shows a power spectrum for a nozzle where the oil and steam are set at normal pressure of 175 but which exhibits unstable and undesirable flow. The pressure is measured at point 10 in FIG. 1. The nozzle is then rodded and cleaned. FIGS. 4(b), 4(c), 4(d) and 4(e) show a power spectra of the nozzle as oil flow is reduced with some steam input until the oil flow is shut off. The pressures, P, are 150, 130, 100 and 20, respectively. There is no chugging. Figure 4(f) shows the power spectrum for the nozzle after normal oil and steam flow are resumed. Pressure is 175 and there is no chugging. FIG. 4(g) shows the power spectrum for the nozzle with the steam shut off and only oil flow. Pressure is 300. FIG. 4(h) shows the power spectrum of the nozzle after normal oil and steam flow are resumed. The pressure, 175 and there is no chugging.

Nozzle malfunctions resulting from an inadequate mixing of feed and steam may be correlated to the various open and closed valves as presented discussed in FIG. 4. These include: partial or complete blockage of the nozzle due to deposits, oil off, steam off, improper proportions of steam to oil, fluctuating flow or chugging, as well as poor atomization, time dependent shifts in flow between two nozzles on the same feed ring as well as physically damaged nozzles. FIGS. 5, is another example of power spectra generated by an accelerometer in contact with the shell of the nozzle corresponding to such states. FIG. 5 shows acceleration power spectra taken for a different feed nozzle under different flow conditions. Pressure is measured at point 10 in FIG. 1.

Figure 5A:
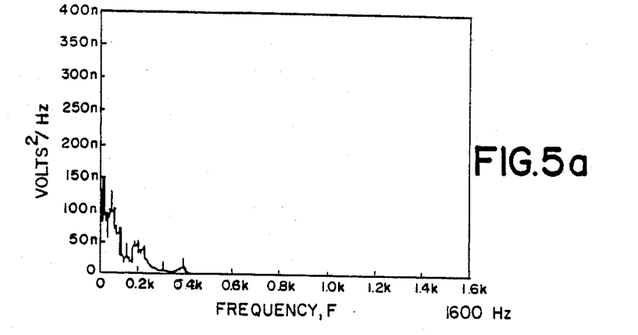
FIGS. 5a-f are other examples of the variation of the power spectrum as the flow conditions of the nozzle vary. The ordinate is in (volts)$^2$/Hz. The abscissa is in Hz. All pressures, P, are in PSI.
Figure 5B:
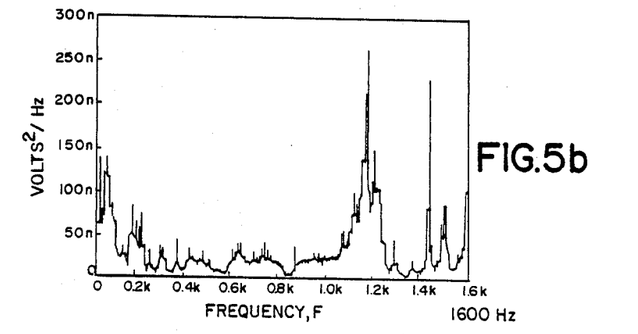
Figure 5C:
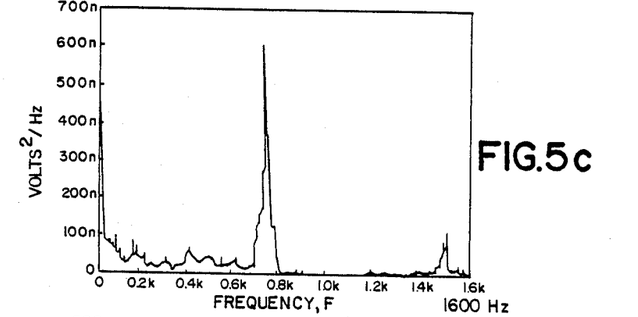
Figure 5D:
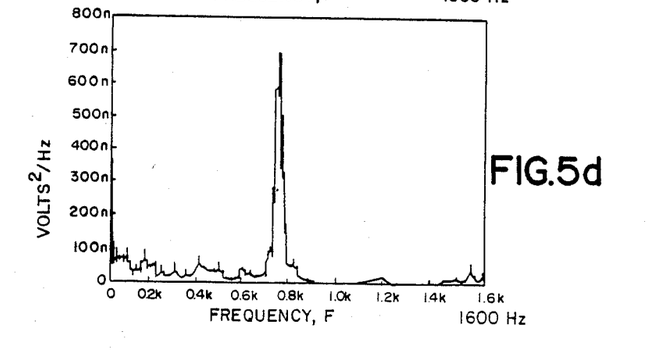
Figure 5E:
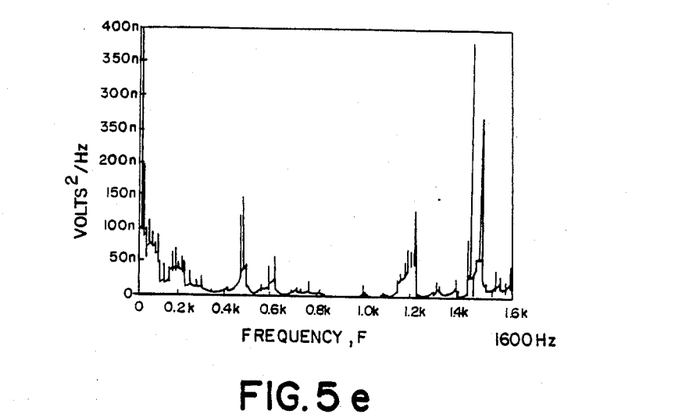
Figure 5F:
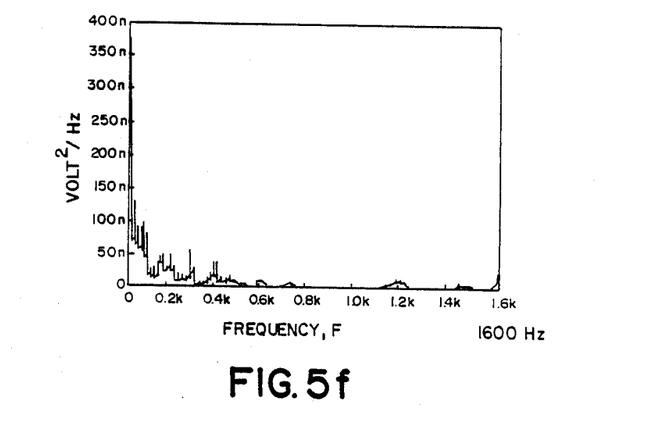
Figure 6A:
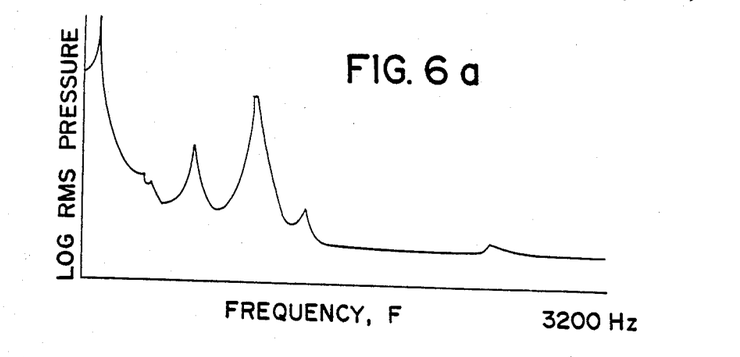
FIGS. 6a-f show the spectra of a nozzle obtained with a pressure transducer for a variety of flow conditions. The ordinate is the log of RMS pressure. The abscissa is in Hz from 0 to 32000 Hz.
Figure 6B:
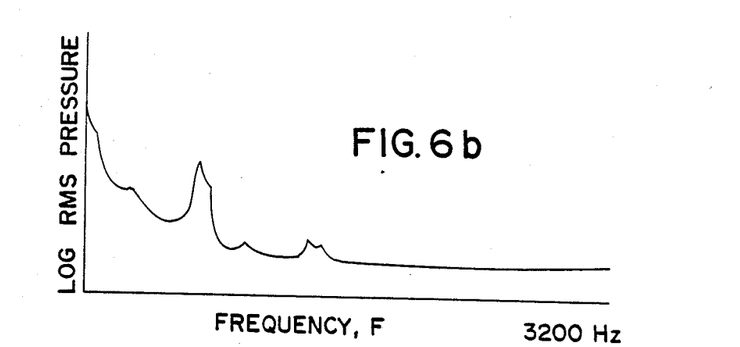
Figure 6C:
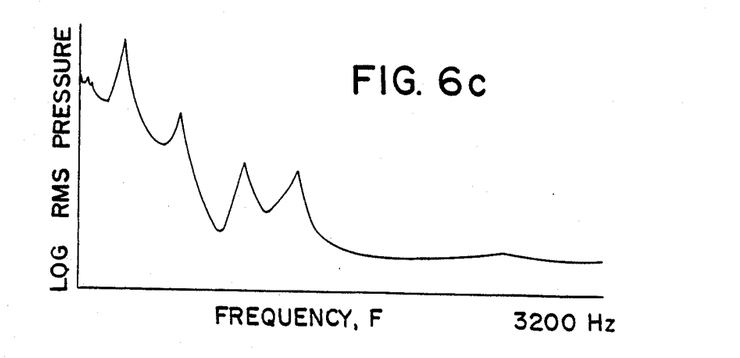
Figure 6D:
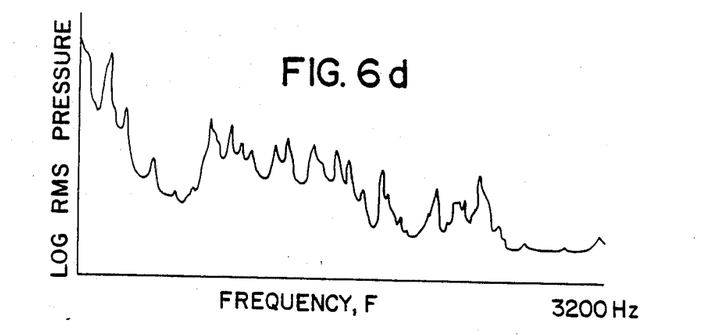
Figure 6E:
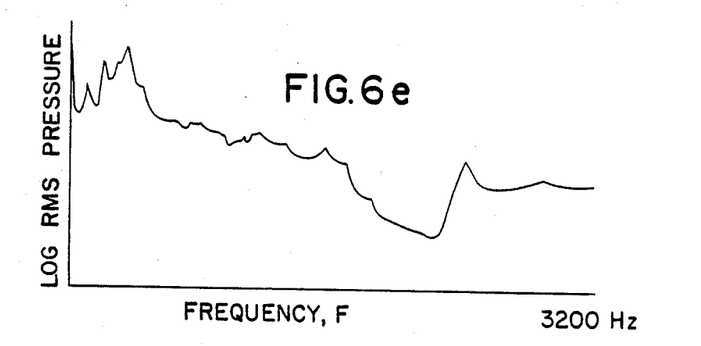
Figure 6F:
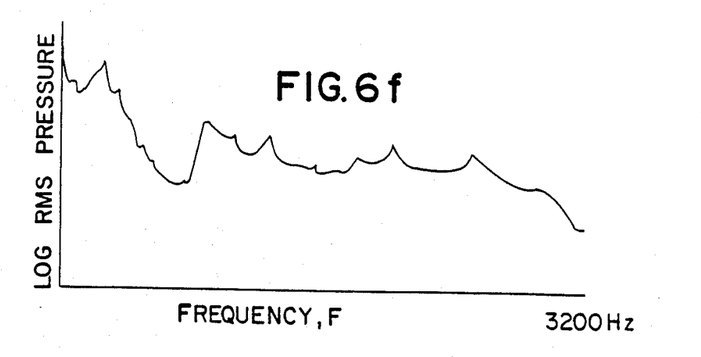

FIG. 5(a) shows the power spectrum for the nozzle while it is plugged (no flow). FIG. 5(b) shows the power spectrum of the nozzle when it is chugging showing unstable flow. The pressure is 183. FIG. 5(c) shows the power spectrum of the nozzle after is has been cleared showing stable flow. The pressure is again 183. FIG. 5(d) shows the power spectrum of the nozzle with only oil flow (steam off). Pressure is 300. FIG. 5(e) shows the power spectrum of the nozzle with only steam flow (oil off). Pressure is 50. FIG. 5(f) shows the power spectrum of the nozzle when another nozzle upstream on the same oil and steam headers is plugged. In this case, pressure is measured at point 12 in FIG. 1. It is important to note that despite differences between the power spectra of FIG. 4 and 5, each is a "fingerprint" of flow states.

An accelerometer will often be the vibrational transducer of choice for generation of the RPS and CPS. However a pressure transducer is an alternative that exhibits some advantages. It is often possible to place the pressure transducer at a location where it can not be inadvertently damaged when cleaning a nozzle. There is no difference in the frequency coverage between an accelerometer and a pressure transducer for the vibratory signals of interest to passive acoustic feed nozzle monitoring. Furthermore, the efficiency of a pressure transducer in contact with the fluid is little affected by a build up of coke or other solids on its active surface since it is acoustic rather that mechanical contact that is important.

As discussed above, a dynamic pressure transducer (8) in contact with the fluid within the feed nozzle at a fixed location on the feed nozzle may be used to obtain a power spectrum. The power spectrum from such a transducer is shown in FIG. 6(a) through 6(f) show the power spectra of a nozzle when it is operating correctly (6a), steam only (6b), same steam, reduced oil (6c), oil, no steam (6d) induced slugging by adding steam (6e) and nozzle instability induced by plugging up-stream nozzle (6f). A log scale is used for these figures to give greater dynamic range.

From the above figures, it is clear that the pressure transducer produces an equally distinct power spectrum to function as a CPS or RPS as does the accelerometer generated power spectrum However the pressure transducer generated power spectrum is simpler in that it contains a smaller number of peaks and hence more changes in it are more readily recognized by either a human observer in the case of periodic nozzle monitoring or by simpler computer pattern recognition algorithm in the case of continuous or real time nozzle monitoring.

The simplicity of the pressure transducer generated power spectrum can be understood if we note that the peaks in the power spectrum arise from resonances in the fluid contained in the bore or ancillary tubing of the feed nozzle which have been excited by broadband noise from the fluid exiting the nozzle tip. The peaks in the power spectrum generated by the accelerometer in contact with the nozzle shell contain as well vibrational resonances associated with the mechanical vibrational modes of the nozzle as well as structural modes of the process vessel Using the concept of acoustic impedance, it is easily shown that the signals produced by resonances in the fluid are favored over other resonances when measure in the fluid by a factor of almost 100. A part from this fact, another advantage for the pressure transducer generated CPS is that it may often be advantageous to use a pressure transducer for convenience of location and protection from unintended damage during nozzle maintenance.

Figure 7A:
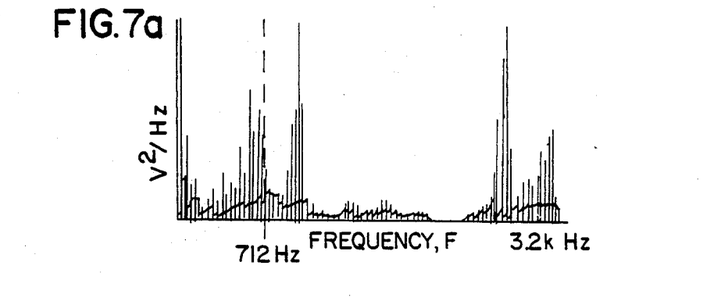
FIGS. 7a and b show the time variation of the vibrating signal and the corresponding power spectrum for the same nozzle conditions.
Figure 7B:
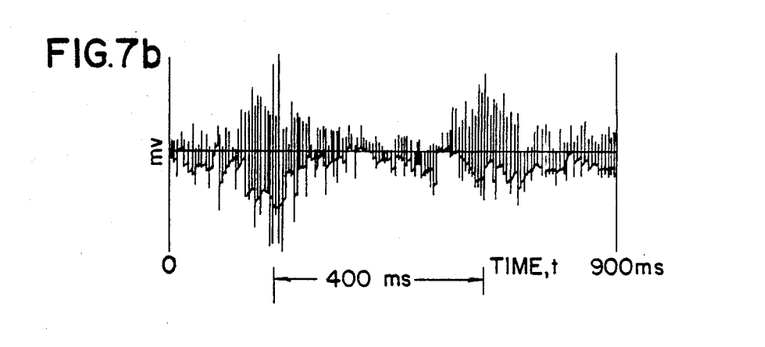
Figure 8A:
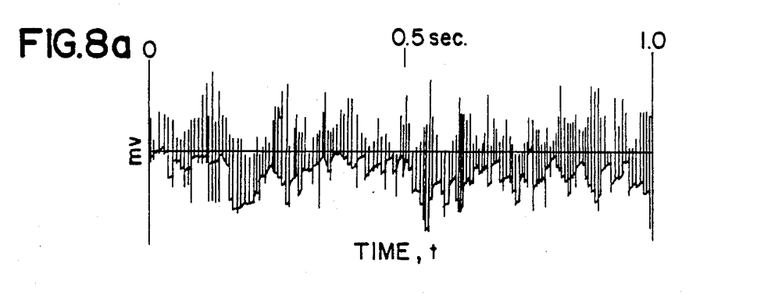
FIGS. 8a and b show the time variation of the vibrating signal for normal oil flow and unstable oil flow.
Figure 8B:
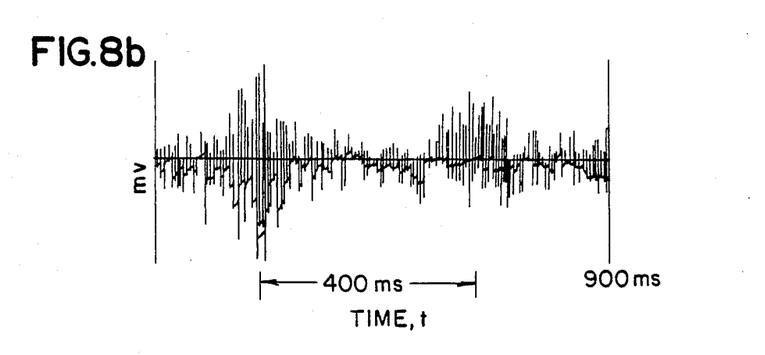

As discussed above, the time variation of the vibrational signal also may be used to obtain information regarding the state of the flow, state of fluid in the nozzle. FIG. 7(b). shows the time variation of the vibrating signal and the corresponding Fourier transform in FIG. 7(a), the power spectrum as a function of frequency for a chugging nozzle. It is sometimes more convenient to use the time variation of the probe signal to detect unstable flow. FIG. 8 compares the time variation for stable oil flow (a) and unstable oil flow, chugging (b).

What is claimed is:
1. A passive acoustic nozzle monitoring process for correcting the operating conditions of a feed nozzle injecting a liquid gas mixture into a process vessel or chamber so as to maintain the correct mixing of said liquid and gas exiting the nozzle comprising:
   determining a Reference Power Spectrum (RPS) showing vibrational resonances from a vibrational resonances from a nozzle when said nozzle is performing at a standard mixing or flow condition which is the desired operating state of the nozzle and where the vibrational resonances that characterize the the flow through the nozzle in the range over which the Power Spectrum is determined,
   (b) determining a current Power Spectrum (CPS) showing vibrational resonances at a later time from said vibrational sensor in close proximity to said nozzle,
   (c) comparing said CPS with said RPS, so as to determine a change in said vibrational resonances, and
   (d) correcting the flow state of the nozzle by changing the variables controlling the relative volumes of gas and liquid entering the nozzle so as to return said nozzle to said desired operating state.
2. The process of claim 1 wherein said vibrational sensor is an accelerometer.
3. The process of claim 1 wherein said vibrational sensor is a dynamic pressure transducer in contact with the fluid mixture in the nozzle.
4. The process of claim 1 further comprising the step of determining a second current Power Spectrum (CPS) and comparing it to said Reference Power Spectrum (RPS) to verify that said nozzle has returned to its desired operating state.
5. The process of claim 1 wherein said RPS and said CPS are time variations of the spectra.
6. The process of claim 1 wherein said RPS and said CPS are frequency variations of the spectra.

* * * * *

UNITED STATES PATENT AND TRADEMARK OFFICE
CERTIFICATE OF CORRECTION

PATENT NO. : 4,824,016
DATED : April 25, 1989
INVENTOR(S) : George D. Cody et al It is certified that error appears in the above-identified patent and that said Letters Patent is hereby corrected as shown below:

Claim 1, column 8, line 29, delete "resonances from a" and insert --sensor in close proximity to said--.

Claim 1, column 8, line 33, after the first "the" and before "the flow through the nozzle in the range" insert --RPS are dominated by the energy associated with--.

Signed and Sealed this

Twenty-sixth Day of June, 1990

*Attest:*

HARRY F. MANBECK, JR.

*Attesting Officer*       *Commissioner of Patents and Trademarks*